US006855342B2

(12) United States Patent
Shacknai et al.

(10) Patent No.: US 6,855,342 B2
(45) Date of Patent: Feb. 15, 2005

(54) COMPOSITIONS AND METHODS FOR HIGH SORPTION OF SKIN MATERIALS AND DELIVERY OF SULFUR

(75) Inventors: Jonah Shacknai, Scottsdale, AZ (US); Eugene H. Gans, Westport, CT (US)

(73) Assignee: Medicis Pharmaceutical Corporation, Scottsdale, AZ (US)

( * ) Notice: Subject to any disclaimer, the term of this patent is extended or adjusted under 35 U.S.C. 154(b) by 52 days.

(21) Appl. No.: 10/022,482

(22) Filed: Dec. 18, 2001

(65) Prior Publication Data

US 2002/0132015 A1 Sep. 19, 2002

Related U.S. Application Data

(63) Continuation-in-part of application No. 09/607,881, filed on Jun. 30, 2000.

(51) Int. Cl.[7] ............................................. A61K 33/04
(52) U.S. Cl. ....................... 424/705; 514/618; 514/886; 514/887
(58) Field of Search ................................ 424/705, 485, 424/117; 514/618, 886, 887

(56) References Cited

U.S. PATENT DOCUMENTS

| | | | |
|---|---|---|---|
| 3,634,264 A | | 1/1972 | Pence |
| 4,388,301 A | * | 6/1983 | Klein ........................ 424/684 |
| 4,587,123 A | | 5/1986 | Price |
| 4,752,472 A | | 6/1988 | Kligman |
| 5,344,971 A | | 9/1994 | Dedieu et al. |
| 6,429,231 B1 | | 8/2002 | Bhagwat et al. |

FOREIGN PATENT DOCUMENTS

| | | | |
|---|---|---|---|
| EP | 0 576 287 A1 | 12/1993 | |
| JP | 03-002124 | 1/1991 | .......... A61K/33/04 |
| WO | WO 82/04393 A1 | 12/1982 | |
| WO | WO 92/05764 | 4/1992 | |
| WO | WO 98/04241 A2 | 2/1998 | |
| WO | WO 98/47466 A3 | 10/1998 | |
| WO | WO 99/24003 A1 | 5/1999 | |

OTHER PUBLICATIONS

Maibach et al., in Journal Of the American Academy of Dermatalogy, vol. 23, No. 1, Jul. 1990, pp 154–155.*
Lin et al.,in Journal Of the American Academy of Dermatology, vol. 18, No. 3, Mar. 1988, pp553–558.*
Skin Care and Cosmetic Ingredients Dictionary, p317 (1994).*
Merck Index pp 697–698, 1288–1289 (1976).*
Harry, R.G., *Harry's Cosmeticology*, pp. 558–561, 6th edition (1973).
Bonnar, et al., "The Demodex Mite Population in Rosacea," Journal of the American Academy of Dermatology, vol. 28, No. 3, Mar. 1993, p. 443–448.
Diaz–Perez, et al., "Demodex mites in Rosacea" and "Reply," Journal of the American Academy of Dermatology, vol. 30, No. 5, Part I, May 1994, p. 812–813.
"Dermatology in General Medicine," 5th ed., CD–ROM, 1999, Chapter 74 p. 1–16.
Lin, et al., "Sulfur Revisited,"Journal of the American Academy of Dermatology, vol. 18. No. 3, Mar. 1988, p. 553–558.
Maibach, et al., "Sulfur Revisited," and "Reply," Journal of the American Academy of Dermatology, vol. 23, No. 1, Jul. 1990, p. 154–156.
Dominey et al., "Papulondular demodicidosis associated with acquired immunodeficiency syndrome," *Journal of the American Academy of Dermatology*, 1989, vol. 20, pp. 197–201.
Ecker, et al., "Demodex Granuloma," *Arch Dermatol*; 1979, vol. 115, pp. 343–344.
Schewach–Miller et al., "Granulomatous rosacea," *Journal of the American Academy of Dermatology*, 1988, vol. 18, No. 6, pp. 1363–1362.
Alexander JO'D., "Hair follicle mite in men," *In Arthropods and Human Skin*, Berlin: Speringer–Verlag, 1984.
Sojka et al, New Polymer Technology for Skin Oil Absorbers and Controlled Release, *Allured's Comsetics & Toiletries*, vol. 114, No. 3 (Mar. 1999), 83–86 and 88.
Database WPI Section Ch, Week 198606 Derwent Publications Ltd., London, GB; AN 1986–040399 XP002245540 & RO 87 009 A (Intr Prod Cosmetice Farmec) May 30, 1985 (abstract).
The Merck Manual, Seventeenth Edition (1999), pp 811–814.
Marks, "Histopathology of Rosacea", Arch. Derm., vol. 100, Dec. 1969 pp 683–691.

* cited by examiner

Primary Examiner—Jyothsna Venkat
(74) Attorney, Agent, or Firm—William J. McNichol, Jr.; Maryellen Feehery; Reed Smith, LLP

(57) ABSTRACT

A composition and method for delivering sulfur to skin and absorbing irritants in the skin. A high sorption base is employed which comprises non-swelling clay, gum, swelling clay, silicon and combinations thereof. The absorption of the irritants does not hinder the delivery of the active ingredient to the skin.

25 Claims, No Drawings

COMPOSITIONS AND METHODS FOR HIGH SORPTION OF SKIN MATERIALS AND DELIVERY OF SULFUR

RELATED APPLICATION

This application is a continuation-in-part of Ser. No. 09/607,881 filed Jun. 30, 2000.

FIELD OF THE INVENTION

The present invention relates to compositions and methods for absorbing the sebum, sweat, and other substances on skin and delivering sulfur can be delivered to the skin, including but not limited to the epidermis, dermis and stratum corneum.

BACKGROUND OF THE INVENTION

Skin may become irritated and certain skin disorders may be exacerbated by materials which accumulate on the skin, including but not limited to sebum (the fatty secretion of the sebaceous glands), sweat, make-up, and dirt, as well as residue from cosmetics and pharmaceuticals applied to the skin (collectively "skin materials"). Patients with skin disorders including but not limited to seborrhea, acne rosacea and acne vulgaris are treated with numerous solutions, lotions and creams. However, the problem of skin irritants, including but not limited to skin materials, persists even during and after use of these treatments.

SUMMARY OF THE INVENTION

This invention provides for sulfur delivery to the skin, including but not limited to stratum corneum, epidermis, and dermis, and its cutaneous absorption, while also absorbing cutaneous irritants (including but not limited to skin materials, such as components of sweat, sebum, moisture, epidermal metabolites, as well as residue from cosmetics and pharmaceuticals applied to the skin). In the prior art, these two actions have been known to oppose each other with absorption action inhibiting the delivery of sulfur or sulfur derivatives.

Sulfur (or elemental sulfur) is a chemically active element. In addition to its elemental form, sulfur forms many compounds. Forms of sulfur suitable for use in the present invention are those forms of elemental sulfur that are known to be useful in dermatological compositions, including but not limited to, colloidal, coated, enrobed, entrapped, fumed, precipitated, washed, and sublimed sulfur, milk of sulfur, and flowers of sulfur. The preferred form of elemental sulfur for use in the present invention is precipitated sulfur.

"Sulfur derivatives" refers to any composition that contains organic or inorganic sulfides, inorganic sulfites, organic or inorganic mercaptans, or any other than is being applied to the skin or hair of a user, including but not limited to cationic sulfur compounds, such as selenium sulfide, potassium sulfide, poly-potassium sulfide, poly-calcium polysulfide, $H_2S$, sulfuric acid, bisulfides, sulfur dioxide, thiols, organic salts, sodium sulfacetamide, or combinations thereof (most preferably sodium sulfacetamide).

Inorganic sulfides suitable for use in connection with the present invention are those inorganic sulfides known to be useful in dermatological compositions and include, but are not limited to, selenium sulfide, sodium thiosulfate as well as those inorganic sulfides having the formula: RS, RSH, $R_2S$, RSSR, or RSSH, wherein R is an inorganic element that can bind ionically or covalently with sulfur.

Organic sulfides suitable for use in connection with the present invention are those organic sulfides known to be useful in dermatological compositions and include, but are not limited to, those organic sulfides having the formula: RS, R2S, RSH, R'SSR', or R'SSH, wherein R' is an organic compound and its salts that can bind ionically or covalently with sulfur. Exemplary organic sulfides include, but are not limited to sodium thioglycolate (sodium mercaptoacetic acid), and gluathione.

Inorganic sulfites suitable for use in the present invention are those inorganic sulfites known to be useful in dermatological compositions, including but not limited to, sulfites and metabisulfites.

The carrier for active ingredients (active ingredients include but are not limited to sulfur and sulfur derivatives) must be "dermatologically acceptable" in the sense of being compatible with the active ingredients and not injurious to the subject. Carriers include those suitable for topical administration and may be prepared by methods known in the art.

Skin is defined to include the epidermis, dermis, stratum corneum or combinations thereof on a mammal, preferably human, cat or dog.

An embodiment of the present invention is a high sorption composition which comprises sulfur and one or more sulfur derivative, and one or more high sorption base. A high sorption base comprises one or more non-swelling clay, one or more gum, one or more swelling clay, one or more silicon, or combinations thereof. The high sorption base allows both the penetration of the sulfur and sulfur derivatives and delivery to the skin, and also absorbs skin irritants (or irritants), including but not limited to skin materials.

Sulfur may be delivered to the skin in a therapeutically effective manner either as elemental sulfur or as a sulfur derivative. Once delivered to the skin, the sulfur or sulfur derivative may act directly or may first be converted to another sulfur-containing chemical entity.

Clay materials are sorptive minerals characterized by low bulk density and layered lattice crystal structures. These minerals are derived from condensed forms of silicic acid, $H_4SiO_4$, where each silicon atom is surrounded by four oxygen atoms inducing a tetrahedral structure. Chains or two-dimensional sheets are formed when the tetrahedral structures are linked together by the sharing of common oxygen atoms. Clay materials are composed of such silica tetrahedral sheets with a central alumina octahedral sheet. The non-swelling clay preferably comprises Kaolin, a hydrated aluminum silicate with an approximate formula $Al_2O_8 \cdot 2SiO_2 \cdot H_2O$, such as Vanclay. Swelling clays are known to swell to a very large extent when the dry clay is contacted with water, and include, smectites for example montmorillonite, bentonite, clinoptilolite, vermiculite, magadite, smectite, laponite, and beidellite, preferably magnesium aluminum silicate, such as Veegum Ultra by R. T. Vanderbilt Company, Inc., Norwalk, Conn.

The gum comprises a natural gum, an artificial gum or a combination thereof, preferably xanthan gum which is a high molecular weight heteropolysaccharide gum produced by a pure-culture fermentation of a carbohydrate with *Xanthomonas campestris*, such as Keltrol CGF by Calgon Corporation, Pittsburgh, Pa.

Silicon means any composition that contains silica, colloidal silica, colloidal hydrated silica, precipitated silica, or silica gels, including but not limited to silicon dioxide.

Another embodiment includes a composition comprising water, xanthan gum, magnesium aluminum silicate, kaolin, silicon dioxide, sodium sulfacetamide, sodium thiosulfate, glyceryl stearate, PEG-100 stearate, quillaia saponaria extract, benzyl alcohol, and sulfur.

DETAILED DESCRIPTION OF THE PREFERRED EMBODIMENTS

The present invention is not to be limited by any mechanism described in the specification, because it is defined by the claims.

One embodiment of the present invention is a composition comprising sulfur, one or more sulfur derivatives, such as sodium sulfacetamide, sulfites, mercaptans or combinations thereof (preferably sodium sulfacetamide), and a pharmaceutically acceptable carrier which comprises a high sorption base. When the composition is deposited on animal skin, preferably human skin, the sulfur and sulfur derivatives may be converted on, within or both on and within the skin surface layers by skin materials, such as sebum, moisture and sweat components into sulfur derivatives. These sulfur derivatives may have antimicrobial, antifungal, antiparasitic or a mixture of benefits. The composition absorbs the irritants such as skin materials.

In another embodiment, a high sorption base comprises one or more non-swelling clays (including but not limited to kaolin), one or more swelling clays (including but not limited to montmorillonite clays, preferably magnesium aluminum silicate, bentonite, hectorite (such as Bentone® 38 which is dimethyldistearyl ammonium hectorite by Rheox, Inc., Hightstown, N.J., and which is a suspending agent/non-surfactant and a solvent/viscosity reducing agent, and surface reactive montmorillonite), (including but not limited to stearalkonium hectorites), one or more natural gums (including but not limited to xanthan gum, guar gum, gum arabic, carrageenan and alginates), one or more non-ionic surfactants (including but not limited to stearates, palmitostearates, glycerides, sorbitan esters, polyoxyethylene ethers, polyoxyethylene glycol esters, $C_{20}$–$C_{24}$ glyceryls and emulsifying waxes) and one or more hydrophilic solvents (including but not limited to water, glycerin, propylene glycol and polyethylene glycol).

One embodiment of the present invention comprises a method for absorbing irritants from the skin and delivering sulfur to the skin. A composition of sulfur, one or more sulfur derivatives, such as sodium sulfacetamide, sulfites, mercaptans or combinations thereof (most preferably sodium sulfacetamide), and a high sorption base with a pH of from about 6.5 to about 8.1 is topically applied to the effected skin. The high sorption base comprises non-swelling clay, gum, swelling clay, silicon or combinations thereof. The non-swelling clay is present preferably at about 15–20%, more preferably at about 18.00% (all percents are weight percents). The gum is present preferably at about 0.20–1.00%, more preferably at about 0.30%. The swelling clay is present preferably at about 1.00–2.00%, more preferably at about 1.50%. The silicon is present preferably at about 0.00–10.00%, more preferably at about 5.00%. The composition is applied to the skin, absorbs irritants from the skin, and delivers sulfur to the skin. The delivered sulfur may be from the sulfur, sulfur derivatives or a combination thereof.

Another embodiment includes a composition comprising water, xanthan gum, magnesium aluminum silicate, kaolin, silicon dioxide, sodium sulfacetamide, sodium thiosulfate, glyceryl stearate, PEG-100 stearate, quillaia saponaria extract (such as Vegetol® Bois de Panama which is a propylene glycol and water mixture or Quillaia Vegetol® GR-038 Hydro by Gattefosse S. A., Saint Priest Cedex, France), benzyl alcohol, and sulfur. The glyceryl stearate and PEG-100 stearate (such as Lipomulse® 165 by Lipo Chemicals, Inc. Paterson, N.J.) have emollient, emulsifying and surfactant qualities. The high sorption base in this invention promotes absorption of irritants but does not inhibit the delivery of the active ingredient, sulfur derivatives, to the skin.

Another embodiment of the invention is a method for enhancing absorption of sulfur in skin. A composition of sulfur, one or more sulfur derivatives, preferably sodium sulfacetamide, sulfites, mercaptans or combinations thereof (most preferably sodium sulfacetamide), and a high sorption base, with a pH of from about 6.5 to about 8.1 is topically applied to the effected skin. The sulfur derivative is preferably present at about 10%–15% by weight. The sulfur may be absorbed in the skin; and may be from the sulfur, sulfur derivatives or combinations thereof.

Another embodiment of the present invention is a method of delivering sulfur (from the sulfur, sulfur derivatives, or combinations thereof in the composition) to the skin and absorbing irritants including but not limited to skin materials from the facial skin of a human subject. A composition of sulfur, one or more sulfur derivatives, preferably sodium sulfacetamide, sulfites, mercaptans or combinations thereof (most preferably sodium sulfacetamide), and a high sorption base with a pH of from about 6.5 to about 8.1 is topically applied to the effected skin. The sulfur is preferably at about 5% and an additional sulfur derivative is preferably present at about 10%.

EXAMPLE 1

One embodiment of the present invention is the following preferred composition.

| CTFA Name | Percent w/w |
| --- | --- |
| Phase A | |
| Purified Water | 41.76 |
| Xanthan Gum NF | 0.30 |
| Phase B | |
| Kaolin USP | 18.00 |
| Silicon Dioxide NF | 5.00 |
| Sulfacetamide Sodium USP | 11.29 |
| Sodium Thiosulfate | 0.10 |
| Phase C | |
| Glyceryl Stearate & PEG-100 Stearate | 10.00 |
| Quillaia Saponaria Extract | 1.00 |
| Benzyl Alcohol NF | 1.00 |
| Phase D | |
| Precipitated Sulfur USP | 5.00 |
| Phase E | |
| Witch Hazel (14% Alcohol) | 5.00 |
| Fragrance 27160 | 0.05 |

EXAMPLE 2

A composition according to the invention containing 5% (radiolabeled) sulfur in addition to sodium sulfacetamide was applied at real-life use levels to the surface of wetted excised human skin mounted in a skin penetration cell. After 12 hours, the skin was rinsed and wiped off, and a second dose was then applied for an additional 12 hours. Then, the radiolabeled sulfur was determined (a) on the surface of and within the stratum corneum; (b) within the epidermis and within the dermis; and (c) within the reservoir (the reservoir was designed to emulate the blood circulation below the skin) underneath the skin which represents the amount passing through the skin.

The present invention in another embodiment may be used to deliver sulfur below the dermis and epidermis and systemically as evidenced in the data regarding the reservoir.

The following table shows the results from this example:

| Micrograms of Sulfur Deposited | | | | |
|---|---|---|---|---|
| On the Stratum Corneum Surface | Within the Stratum Corneum | In the Epidermis | In the Dermis | In the Reservoir |
| 1344 | 295 | 117 | 27 | 26 |

Over 25% of the applied dose of sulfur has been absorbed below the surface of the stratum corneum. These are the critical areas because lesions and inflammation occur in the stratum corneum, epidermis and dermis, and the composition is useful for treatment and prevention of lesions and inflammation.

EXAMPLE 3

Four high sorption treatment formulations, containing radio-labeled sulfur ($S^{35}$), which are set forth in the following tables, in addition to sodium sulfacetamide, were applied at real-life use levels to the surface of wetted, excised human skin mounted in a skin penetration cell. Each treatment was left on the skin for 20 minutes before being rinsed and wiped off once. After 12 hours, a second dose of each formulation was then applied for an additional 20 minutes, then rinsed and wiped off once.

At 24 hours, the skin was removed from each cell and the amount of radio-labeled sulfur was determined: (a) on the surface of and within the stratum corneum; (b) within the epidermis and within the dermis; and (c) within the reservoir underneath the skin which represents the amount passing through the skin.

| | Percent w/w |
|---|---|
| Formula A | |
| CTFA Name | |
| Purified Water | 41.76 |
| Xanthan Gum NF | 0.30 |
| Magnesium Aluminum Silicate | 1.50 |
| Kaolin USP | 18.00 |
| Silicon Dioxide NF | 5.00 |
| Sulfacetamide Sodium USP | 11.29 |
| Sodium Thiosulfate | 0.10 |
| Glyceryl Stearate & PEG-100 Stearate | 10.00 |
| Quillaia Saponaria Extract | 1.00 |
| Benzyl Alcohol NF | 1.00 |
| Precipitated Sulfur USP | 5.00 |
| Witch Hazel (14% alcohol) | 5.00 |
| Fragrance 27160 | 0.05 |
| Formula B | |
| CTFA | |
| Distilled water | 41.76 |
| Xanthan Gum NF | 0.30 |
| Magnesium Aluminum Silicate | 1.50 |
| Glyceryl Stearate & PEG 100 Stearate | 10.00 |
| Quillaia Extract | 1.00 |
| Benzyl Alcohol | 1.00 |
| Kaolin USP | 18.00 |
| Silicon Dioxide | 2.00 |
| Sulfacetamide Sodium USP | 11.29 |
| Sodium Thiosulfate | 0.10 |
| Precipitated Sulfur USP | 5.00 |
| Silicon Dioxide | 3.00 |
| Witch Hazel (14% alcohol) | 5.00 |
| Fragrance 27160 | 0.05 |
| Formula C | |
| CTFA | |
| Distilled Water | 46.76 |
| Xanthan Gum NF | 0.30 |
| Magnesium Aluminum Silicate | 1.50 |
| Glyceryl Stearate & PEG 100 Stearate | 10.00 |
| Quillaia Saponaria Extract (e.g. Vegetol ® Bois de Panama) | 1.00 |
| Benzyl Alcohol NF | 1.00 |
| Kaolin USP | 18.00 |
| Sulfacetamide Sodium USP | 11.29 |
| Sodium Thiosulfate | 0.10 |
| Precipitated Sulfur | 5.00 |
| Witch Hazel (14% alcohol) | 5.00 |
| Fragrance 27160 | 0.50 |
| Formula D | |
| CTFA | |
| Distilled water | 46.76 |
| Xanthan gum NF | 0.30 |
| Magnesium Aluminum Silicate | 1.50 |
| Glyceryl Stearate & PEG 100 Stearate | 10.00 |
| Quillaia saponaria extract (e.g. Vegetol ® Bois de Panama) | 1.00 |
| Benzyl alcohol NF | 1.00 |
| Kaolin USP | 16.00 |
| Hectorite (e.g. Bentone ® 38) | 2.00 |
| Sulfacetamide Sodium USP | 11.29 |
| Sodium Thiosulfate | 0.10 |
| Precipitated Sulfur | 5.00 |
| Witch Hazel (14% alcohol) | 5.00 |
| Fragrance 27160 | 0.05 |

The following table displays the data in micrograms of sulfur delivered to the skin by the four high sorption formulations.

| | On Stratum Corneum Surface | Within the Stratum Corneum | In the Epidermis | In the Dermis | In the Reservoir |
|---|---|---|---|---|---|
| A | 9.6 | 14.4 | 22.0 | 5.7 | 5.5 |
| B | 21.5 | 14.6 | 13.2 | 4.5 | 5.0 |
| C | 24.2 | 10.4 | 21.0 | 4.9 | 5.6 |
| D | 9.7 | 13.3 | 13.0 | 3.7 | 4.5 |

The sulfur released by each of the formulations was substantial and readily measurable.

Finally, except for the amounts of sulfur left on the stratum corneum's surface which were not absorbed or bioavailable, there is little difference between Formula A, and Formula B, C and D. Thus, the high absorbency formulations did not impair the cutaneous bioavailability of sulfur.

It is understood that while the invention has been described in conjunction with the detailed description thereof, that the foregoing description is intended to illustrate and not limit the scope of the invention, which is defined by the scope of the appended claims. Other aspects, advantages, and modifications are evident from a review of the following claims.

What is claimed is:

1. A method for absorbing irritants in the skin and delivering sulfur to skin comprising
    Applying a composition, wherein the composition comprises water, xanthan gum, magnesium aluminum silicate, kaolin, silicon dioxide, at about 10% sodium sulfacetamide, sodium thiosulfate, glyceryl stearate, PEG-100 stearate, quillaia saponaria extract, benzyl alcohol and at about 5% sulfur;
    Absorbing irritants from the skin with the composition; and
    Delivering sulfur to the skin, wherein the skin comprises one or more selected from the group consisting of epidermis, dermis, and stratum corneum.

2. The method of claim 1 wherein the composition has a pH of about 6.5 to about 8.1.

3. The method of claim 1 wherein the composition has a pH of about 7.0 to about 8.1.

4. The method of claim 1 wherein the composition has a pH of about 7.7 to about 8.1.

5. The method of claim 1 wherein the composition has a pH of about 7.3 to about 7.7.

6. The method of claim 1 wherein the xanthan gum is present at about 0.30%.

7. The method of claim 1 wherein the magnesium aluminum, silicate is present at about 1.50%.

8. The method of claim 1 wherein the silicon dioxide is present at about 5.00%.

9. The method of claim 1 wherein the water is present at about 40–50%.

10. The method of claim 1 wherein the water is present at about 41.76%.

11. The method of claim 1 wherein the water is present at about 46.76%.

12. The method of claim 1 wherein the irritants comprise one or more selected from the group consisting of sweat, sebum, moisture, epidermal metabolites, residue from cosmetics and residue from pharmaceuticals.

13. A composition comprising
    Water;
    Xanthan gum;
    Magnesium aluminum silicate;
    Kaolin;
    Silicon dioxide;
    At about 10% Sodium sulfacetamide;
    Sodium thiosulfate;
    Glyceryl stearate;
    PEG-100 Stearate;
    Quillaia saponaria extract;
    Benzyl alcohol; and
    At about 5% Sulfur.

14. The composition of claim 13 has a pH of about 6.5 to about 8.1.

15. The composition of claim 13 has a pH of about 7.0 to about 8.1.

16. The composition of claim 13 has a pH of about 7.7 to about 8.1.

17. The composition of claim 13 has a pH of about 7.3 to about 7.7.

18. The composition of claim 13 wherein the kaolin is present at about 18.00%.

19. The composition of claim 13 wherein the xanthan gum is present at about 0.30%.

20. The composition of claim 13 wherein the magnesium aluminum silicate is present at about 1.50%.

21. The composition of claim 13 wherein the silicon dioxide is present at about 5.00%.

22. The composition of claim 13 wherein the water is present at about 40–50%.

23. The composition of claim 13 wherein the water is present at about 41.76%.

24. The composition of claim 13 wherein the water is present at about 46.76%.

25. A method for delivering sulfur to skin and absorbing irritants in the skin comprising:
    Applying a composition, wherein the composition comprises water, xanthan gum, magnesium aluminum silicate, kaolin, silicon dioxide, at about 10% sodium sulfacetamide, sodium thiosulfate, glyceryl stearate, PEG-100 stearate, quillaia saponaria extract, benzyl alcohol and at about 5% sulfur;
    Absorbing irritants from the skin with the composition wherein the irritants comprise one or more selected from the group consisting of sweat, sebum, moisture, epidermal metabolites, residue from cosmetics and residue from pharmaceuticals; and
    Delivering sulfur to the skin, wherein the skin comprises one or more selected from the group consisting of epidermis, dermis and stratum corneum.

* * * * *